(12) United States Patent
Peterson et al.

(10) Patent No.: US 12,080,031 B2
(45) Date of Patent: Sep. 3, 2024

(54) EXTRACTION OF GAS BASED ON IMAGE ANALYSIS

(71) Applicant: California Bioenergy LLC, Dallas, TX (US)

(72) Inventors: Keith Peterson, Dallas, TX (US); Thomas Perkins, Dallas, TX (US)

(73) Assignee: California Bioenergy LLC, Dallas, TX (US)

( * ) Notice: Subject to any disclaimer, the term of this patent is extended or adjusted under 35 U.S.C. 154(b) by 391 days.

(21) Appl. No.: 17/672,189

(22) Filed: Feb. 15, 2022

(65) Prior Publication Data

US 2023/0260160 A1  Aug. 17, 2023

(51) Int. Cl.
| | |
|---|---|
| *G06T 7/90* | (2017.01) |
| *C12M 1/00* | (2006.01) |
| *C12M 1/107* | (2006.01) |
| *C12M 1/36* | (2006.01) |

(52) U.S. Cl.
CPC ............... *G06T 7/90* (2017.01); *C12M 21/04* (2013.01); *C12M 23/26* (2013.01); *C12M 23/38* (2013.01); *C12M 41/48* (2013.01); *G06T 2207/30108* (2013.01)

(58) Field of Classification Search
CPC ............. G06T 7/90; G06T 2207/30108; G06T 2207/10024; G06T 7/73; C12M 21/04; C12M 23/26; C12M 23/38; C12M 41/48; Y02E 50/30

USPC .......................................................... 382/141
See application file for complete search history.

(56) References Cited

U.S. PATENT DOCUMENTS

| | | | | |
|---|---|---|---|---|
| 9,688,585 | B2 * | 6/2017 | Efrati | ............... C12M 23/26 |
| 2015/0355081 | A1 * | 12/2015 | Phillips | ............... G01N 21/45 |
| | | | | 356/451 |
| 2020/0254387 | A1 * | 8/2020 | Buckenham | ............. A01C 3/00 |

* cited by examiner

*Primary Examiner* — Neil R McLean
(74) *Attorney, Agent, or Firm* — Stephen Y. Liu; David W. Carstens; Carstens, Allen & Gourley, LLP

(57) ABSTRACT

A method and apparatus for biogas extraction. The method includes obtaining a set of images that includes a field of view encompassing at least a portion of the flexible roof and a background; generating a sample region having a first end overlapping only the flexible roof and a second end overlapping only the background; determining an average pixel color of an end slice located at the first end or the second end of the sample region; determining, based on the average pixel color of the end slice of the sample region, a fill percentage of the sample region attributed to an object overlapped by the end slice; estimating an amount of inflation of the flexible roof based on the fill percentage and a correlation between fill percentages of the sample region and predetermined amounts of inflation included in calibration data; and controlling extraction of the biogas based on the estimation.

20 Claims, 9 Drawing Sheets

| OBJECT FILL PERCENTAGE DATA | BIOGAS VOLUME DATA | ROOF INFLATION ESTIMATE DATA |
|---|---|---|
| 10% | 0 m$^3$ | 0% |
| 30% | 2,500 m$^3$ | 25% |
| 45% | 5,000 m$^3$ | 50% |
| 55% | 7,500 m$^3$ | 75% |
| 60% | 10,000 m$^3$ | 100% |

EXTRACTION OF GAS BASED ON IMAGE ANALYSIS

BACKGROUND OF THE INVENTION

Technical Field

The present invention relates to management of biogas digesters, and more specifically, to a system and method for controlling the extraction of biogas from lagoon-type digesters covered by a flexible roof based on image analysis.

Description of Related Art

Biogas is a mixture of gasses that primarily includes methane and carbon dioxide, as well as small amounts of hydrogen sulfide. Biogas is typically formed in a digester from the anaerobic decomposition of organic waste material by anaerobic organisms. Organic waste material can include livestock manure, food processing waste, and agricultural residues. When captured, biogas can be purified to form a renewable natural gas (RNG) that is about 95% methane, which can be used to generate power in a methane-burning power plant or used as fuel for vehicles powered by compressed natural gas (CNG).

Biogas can be produced in batch processes or continuous flow processes at a particular temperature range dictated by the type of anaerobic microbes selected for biomass digestion and using different types of digesters. One commonly used digester is a covered lagoon that generally includes a lined earthen pit covered with a flexible roof. Organic waste material can be pumped into the lagoon and optionally inoculated with anaerobic microbes to form biogas and digestate. The biogas is captured by the flexible roof, which expands and contracts based on the volume of biogas produced. Digestate and biogas can be periodically pumped out of the covered lagoon and processed in one or more downstream unit operations to form various commercial products.

SUMMARY OF THE INVENTION

Novel aspects of the present disclosure are directed to a method for controlling biogas extraction. The method includes steps of obtaining a set of images that includes a field of view encompassing at least a portion of the flexible roof and a background; generating a sample region having a first end that overlaps only the flexible roof and a second end that overlaps only the background; determining an average pixel color of an end slice of the sample region that is located at the first end or the second end of the sample region; determining, based on the average pixel color of the end slice of the sample region, a fill percentage of the sample region attributed to an object overlapped by the end slice; estimating an amount of inflation of the flexible roof based on the fill percentage and a correlation between fill percentages of the sample region and predetermined amounts of inflation included in calibration data; and controlling extraction of the biogas based on the estimated amount of inflation.

Novel aspects of the present disclosure are also directed to an apparatus for controlling biogas extraction. The apparatus includes a processor and a memory operatively connected with the processor. The memory stores instructions that, when executed by the processor, causes the apparatus to obtain a set of images that includes a field of view encompassing at least a portion of the flexible roof and a background; generate a sample region having a first end that overlaps only the flexible roof and a second end that overlaps only the background; determine an average pixel color of an end slice of the sample region that is located at the first end or the second end of the sample region; determine, based on the average pixel color of the end slice of the sample region, a fill percentage of the sample region attributed to an object overlapped by the end slice; estimate an amount of inflation of the flexible roof based on the fill percentage and a correlation between fill percentages of the sample region and predetermined amounts of inflation included in calibration data; and control extraction of the biogas based on the estimated amount of inflation.

BRIEF DESCRIPTIONS OF THE DRAWINGS

The novel features believed characteristic of the invention are set forth in the appended claims. The invention itself, however, as well as a preferred mode of use, further objectives, and advantages thereof, will be best understood by reference to the following detailed description of illustrative embodiments when read in conjunction with the accompanying drawings, wherein:

DETAILED DESCRIPTION OF THE INVENTION

Figure 1:
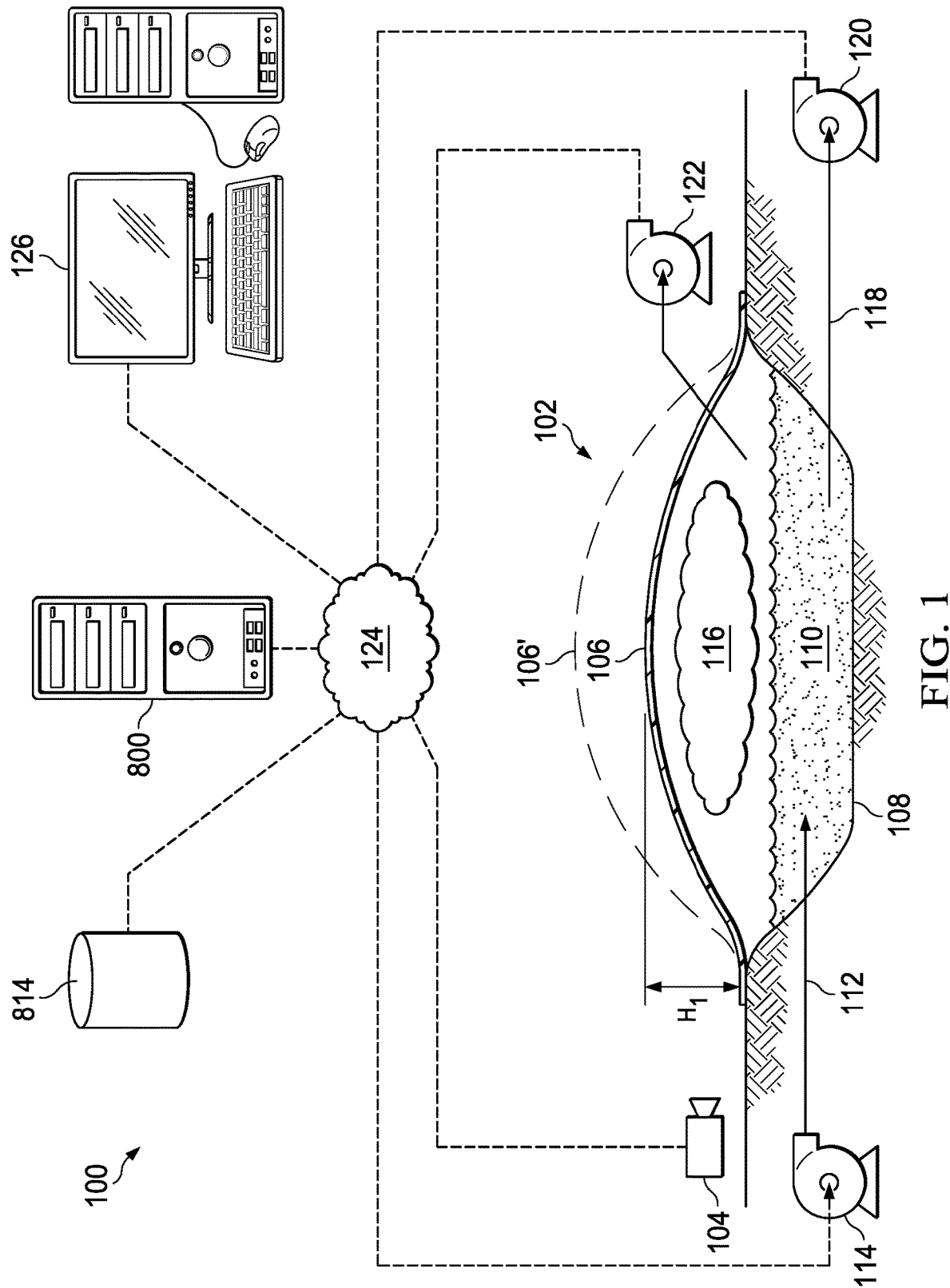
FIG. 1 is a schematic diagram of a system utilizing image analysis for extraction of biogas from a digester according to an illustrative embodiment.

Several embodiments incorporating novel aspects of the disclosure will now be described with reference to the drawings. Unless otherwise noted, like elements will be identified by identical numbers throughout all figures. The invention illustratively disclosed herein suitably may be practiced in the absence of any element which is not specifically disclosed herein.

One problem unique to covered lagoon digesters is managing the amount of inflation of the floating roof to prevent overinflation and underinflation. Because the floating roof is often formed from a polymeric membrane, overinflation of the flexible roof can cause the flexible roof to burst. Replacement of the floating roof, which can be hundreds of square feet in size, is expensive and time-consuming. Underinflation of the flexible roof can cause at least a portion of the flexible roof to float on the surface of biomass contained in the lagoon, which in turn can cause uptake of the biomass by air compressors, causing fouling that necessitates costly cleaning and repair or replacement. Because the flexible roof lacks a consistent structure or form, the amount of inflation of the flexible roof, which is a function of the volume of gas captured underneath, can be unpredictable.

To prevent overinflation or underinflation of the floating cover, biogas is selectively pumped out of the digester. The rate of biogas production in a covered lagoon can vary depending upon a number of factors, such as ambient temperature and composition of the organic waste material that forms the biomass, which means that biogas extraction from the covered lagoon cannot be effectively automated by a timer. One conventional method controlling the amount of inflation of the flexible roof involves sending an operator onsite to physically observe the amount of inflation of the flexible roof before activating a set of air compressors for extracting biogas. As used herein, the term "set" means one or more. Thus, a set of air compressors can mean one air compressor or two or more air compressors. This conventional method is time-consuming because facilities housing covered lagoons are typically spread out over large tracts of land, and facilities are often located in geographically isolated locations. Accordingly, novel aspects of this disclosure recognize the need to be able to estimate the amount of inflation of a flexible roof of a covered lagoon quickly and efficiently to control the extraction of biogas, and without the need for operators to be physically onsite, which is more efficient and cost-effective.

Extraction of biogas data according to novel aspects of this disclosure can be facilitated by execution of an inflation estimation program referencing calibration data generated during an initial calibration process. During the calibration process, images taken of the flexible roof of a digester are analyzed, and the results are correlated with amounts of inflation of the flexible roof. As used herein, the term "amount of inflation" can mean an estimated amount of biogas contained within the digester under the flexible roof or an estimated inflation percentage of the flexible roof, i.e., any percentage between 0% full (completely empty) and 100% full (completely full). Once the calibration data has been generated, an operator can run the inflation estimation program to determine the real-time amount of inflation of the flexible roof without the need for personnel onsite. The real-time amount of inflation can be used to efficiently control biogas extraction from the digester. As an added benefit, the real-time amount of inflation of the flexible roof of the digester can be used to determine the biogas inventory in each of the digesters of a biogas production facility and in the biogas production facility as a whole.

FIG. 1 depicts a schematic diagram of a system utilizing image analysis for controlling biogas extraction from a digester according to an illustrative embodiment. Generally, the system 100 utilizes an inflation estimation program to estimate the amount of inflation of the flexible roof of digester 102 based on calibration data generated during a calibration process. The calibration data correlates image data derived from a series of images captured by camera 104 with predetermined amounts of inflation of the flexible roof 106 of the digester 102. Once the calibration data has been generated, subsequent images captured by the camera 104 can be analyzed by the inflation estimation program to determine an amount of inflation of the flexible roof 106, which can then be used to manage the extraction of biogas from the digester 102.

In this exemplary embodiment in FIG. 1, the digester 102 is depicted as a lagoon 108, i.e., a lined pit covered by a flexible roof 106. Biomass 110 is pumped into the lagoon 108 as influent 112 by pump 114 and maintained in the lagoon 108 to undergo anaerobic decomposition to form biogas 116 and digestate. The digestate is pumped out of the lagoon 108 as effluent 118 by pump 120, or in another embodiment, the digestate is permitted to flow into another, lower-elevation lagoon by gravity. As biogas 116 is collected under the flexible roof 106, the flexible roof 106 expands upwardly to achieve a bulging shape represented by dashed line 106'. The biogas 116 is collected under the flexible roof 106 and periodically extracted by operation of an air compressor 122. The biogas 116 can be conveyed to downstream unit operations (not shown) for energy production or conversion into a natural gas product, such as RNG. The onsite equipment, e.g., camera 104, pumps 114 and 120, and air compressor 122, can be controlled remotely or locally to allow for timely extraction of the biogas 116, which prevents overinflation or underinflation of the flexible roof 106.

Figure 2:
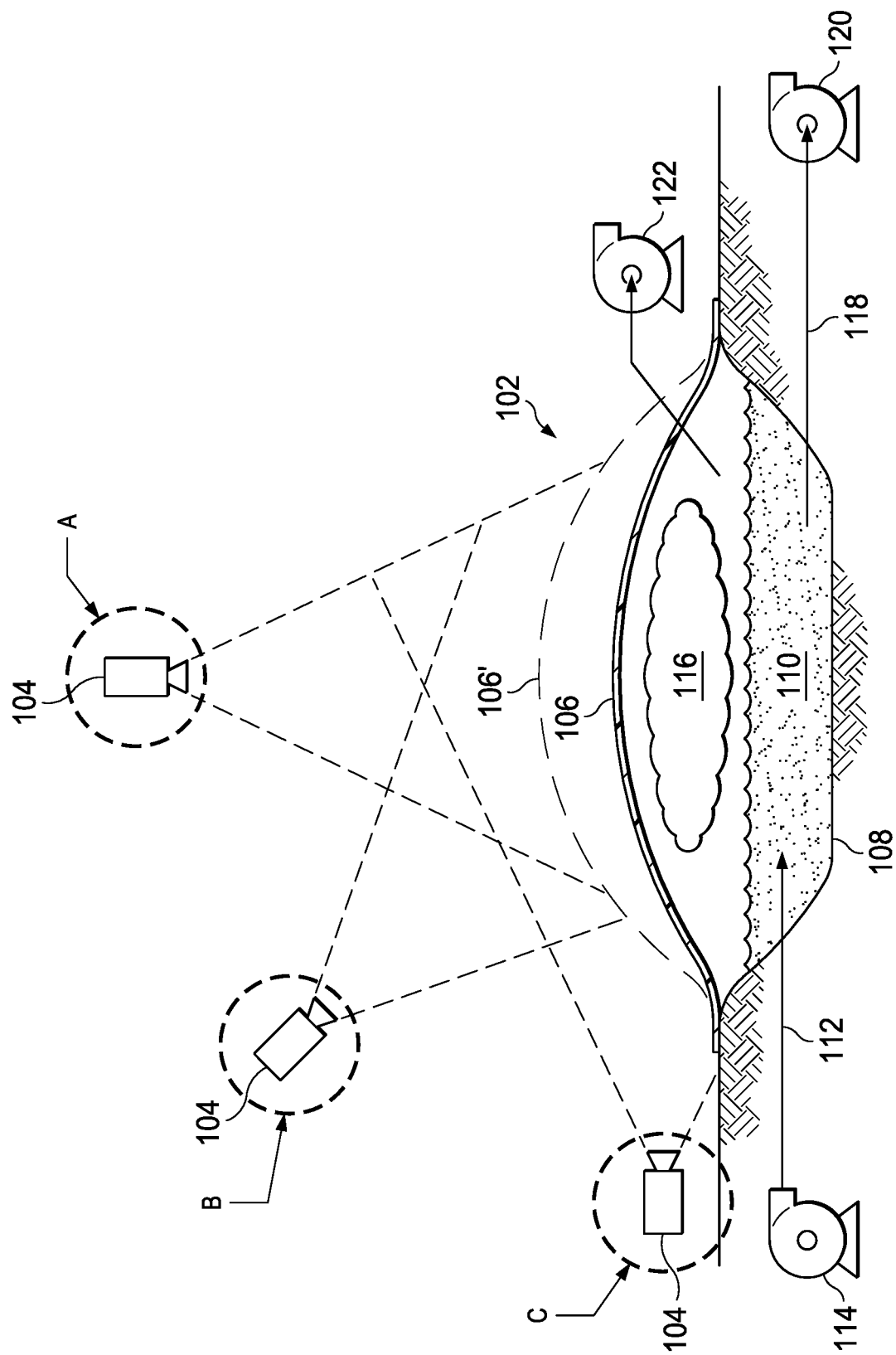
FIG. 2 is a schematic diagram depicting camera placement angles for capturing images usable in the extraction of biogas from a digester according to an illustrative embodiment.
Figure 3:
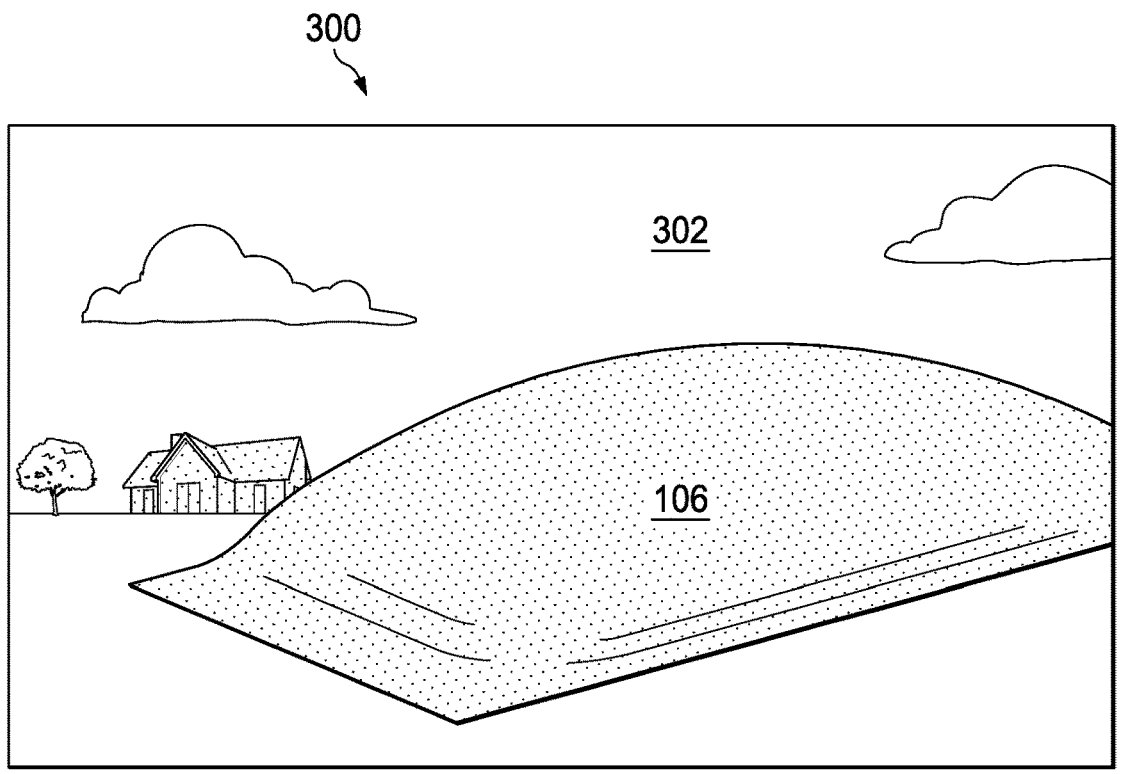
FIG. 3 is a schematic diagram depicting a field of view captured by a camera for extraction of biogas from a digester according to an illustrative embodiment.

In one embodiment, the system 100 includes a camera 104 placed in the vicinity of the digester 102 to capture an image having a field of view that includes the flexible roof 106 and a portion of the background behind the flexible roof 302, which may include terrain or artifacts such as structure 304, as can be seen in FIG. 3. Placement of the camera 104 is described in FIG. 2, and an exemplary field of view captured by the camera 104 is shown and discussed in more detail in FIG. 3. Images captured by the camera 104 can be analyzed by an inflation estimation program 804, depicted in FIG. 8, to develop calibration data that correlates one or more objects in the image and a predetermined amount of inflation of the flexible roof 106. In a non-limiting embodiment, the one or more objects in the image can be the flexible roof 106 and/or a background of the flexible roof 302. The calibration data can then be used by the inflation estimation program 804 to determine the amount of inflation of the flexible roof 106, which can then be used for managing extraction of biogas 116 from the digester 102.

The inflation estimation program 804 is a software program that can be hosted in a computing device located onsite at the biogas production facility or at a location remote from the biogas production facility, i.e., in computing device 800 or in client device 126. The computing device 800 can also include various input/output devices that allow for calibrating the inflation estimation program 804 and optionally for monitoring and control of the onsite equipment, e.g., the pumps 114 and 120 and air compressor 122, at the biogas production facility. In this illustrative embodiment, the inflation estimation program 804 is hosted on a computing device 800 located remotely to the biogas production facility and accessible via network 124. Additionally, system 100 includes remote client computing device 126, which can be operated by a user for remotely controlling onsite equipment, for hosting the inflation estimation program 804, and/or for interacting with the inflation estimation program 804, e.g., calibrating the inflation estimation program 804 and receiving output from the inflation estimation program 804 for controlling extraction of biogas 116 from digester 102.

FIG. 2 is a schematic diagram depicting camera placement angles for capturing images usable in the extraction of biogas from a digester according to an illustrative embodiment. Placement of the camera 104 is dictated by the desired composition of objects to be captured in a field of view of the camera 104. In particular, the field of view should show the change in shape of the flexible roof 106 as the volume of captured biogas 116 changes. In one or more embodiments, the field of view also includes a portion of the background 302, as described in more detail in FIG. 3.

Placement of the camera 104 at location A captures a field of view that provides a plan view of the digester 102. The amount of inflation of the flexible roof 106 would be difficult to discern from images captured with the corresponding field of view because inflation and deflation of the flexible roof 106 generally occurs in the upwardly and downwardly direction, i.e., within the perimeter of the digester 102.

Placement of the camera 104 at location B provides a downward perspective view of the digester 102, and placement of the camera 104 at location A provides a side elevation view of the digester 102. The corresponding fields of view captured at each of these camera placement angles can show a change in shape of the flexible roof 106 as the volume of biogas 116 captured under flexible roof 106 causes the shape of the flexible roof 106 to change. However, at camera location B, the composition of objects captured in the field of view includes the flexible roof 106 in the foreground and the ground surrounding the digester 102 in the background. Because image analysis for automatically controlling biogas extraction from digesters is based on color, insufficient contrast between the ground surrounding the digester 102 and the flexible roof 106, particularly in the presence of shadows, may cause difficulty in discerning an amount of inflation of the flexible roof 106 with the camera at location B. Placement of the camera at location A provides the composition of objects captured in the field of view that includes the flexible roof 106 in the foreground and the sky in the background, which may provide adequate contrast for discerning an amount of inflation of the flexible roof 106.

FIG. 3 is a schematic diagram depicting a field of view captured by a camera for extraction of biogas from a digester according to an illustrative embodiment. The composition of objects within the field of view 300 facilitates determination of a relative amount of inflation and/or deflation of the flexible roof 106. In this non-limiting embodiment, the flexible roof 106 of the digester 102 is in the foreground, and the background 302 includes the sky, which corresponds to the field of view captured by a camera placed approximately at location A in FIG. 2.

Image analysis performed on the entirety of an image of the field of view 300 for determining the amount of inflation of the flexible roof 106 can include pixels that uncorrelated to variation attributable to a change in volume of gas under the flexible roof 106. Thus, in one embodiment, image analysis is performed only on a portion of an image of the field of view 300, i.e., within a sample region, as described in more detail in the following figure.

Figure 4:
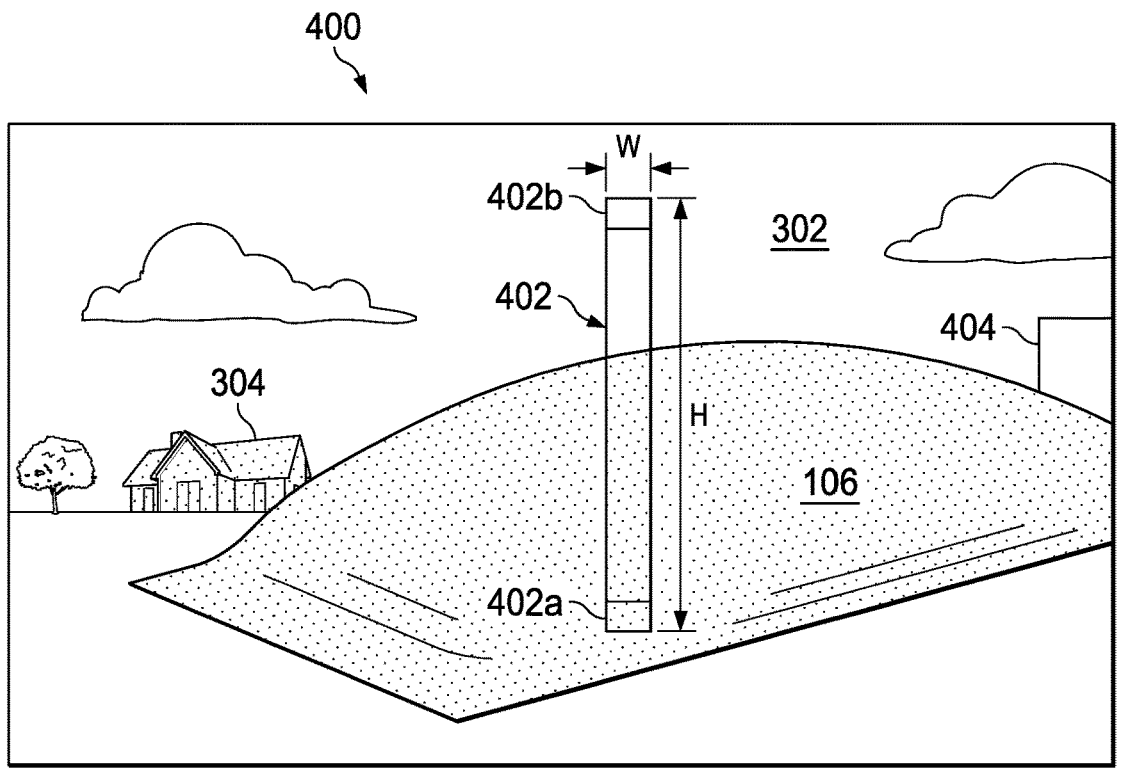
FIG. 4 is a schematic diagram depicting placement of a sample region in an image captured by the camera for the extraction of biogas from a digester according to an illustrative embodiment.

FIG. 4 is a schematic diagram depicting placement of a sample region in an image captured by the camera for the extraction of biogas from a digester according to an illustrative embodiment. The sample region 402 is sub-region of the image 400. The dimensions of the sample region 402 can be some predetermined, default value, or user-defined. The user can be the operator or another individual located onsite at the biogas production facility or remote from the biogas production facility, e.g., operating client computing device 126. If defined by a user, the dimensions can be selected by providing a reference point and dimensional parameters. For example, if the sample region 402 is a rectangle, then the reference point can be a corner of the sample region 402, and the dimensional parameters can be a height and width. In another example, if the sample region 402 is an ellipse, then the reference point can be a center point, and the dimensional parameters can be a minor axis and a major axis. In this illustrative embodiment, the sample region 402 is a rectangle with a width W and height H and oriented with the sides of height H oriented vertically within the image 400. In other embodiments, the sample region 402 can be positioned at an angle relative to vertical. For example, the sample region 402 can have sides of height H oriented at a 45° angle relative to vertical.

In one embodiment, the amount of inflation of the flexible roof 106 is determined by the relative amount of the sample region 402 occupied by the flexible roof 106, i.e., a fill percentage of the sample region 402 attributed to the flexible roof 106. In another embodiment, the amount of inflation of the flexible roof 106 is determined by the relative amount of the sample region 402 occupied by the background 302, which can include terrain, foliage, and other artifacts, such as structure 304. In another embodiment, the amount of inflation of the flexible roof 106 is determined from the fill percentages of both the flexible roof 106 and the background 302. Regardless, the relative amount of an object within the sample region, i.e., the flexible roof 106 and/or the background 302, can be determined based on pixel color. An average pixel color can be determined for the flexible roof 106 and/or the background 302. The average pixel color(s) can then be compared with pixels within sample region 402 to determine the relative amount of an object, i.e., the flexible roof 106 and/or the background 302, within the sample region 402.

In one embodiment, an average pixel color(s) is determined with reference to a sample region 402 positioned within the image 400, which has a first end 402a overlapping only the flexible roof 106 and a second end 402b not overlapping the flexible roof 106. In this illustrative embodiment in FIG. 4, the second end 402b of the sample region 402 overlaps only the background 302. Dimensions for at least one end slice, i.e., a first end slice 402a' and/or a second end slice 402b', of the sample region 402 are established, either by using default values or by user-selection. End slices 402a' and 402b' are geometric shapes that each enclose a plurality of pixels at respective ends of the sample region 402. As discussed in more detail in FIG. 5, the pixels enclosed by the first end slice 402a' correspond to the flexible roof 106 and the pixels enclosed by the second end slice 402b' correspond to the background 302.

In some embodiments, the dimensions of the sample region 402, the placement of the sample region 402 within the image 400, and the dimensions of the first end slice 402a' and the second end slice 402b' should be selected so that the first end slice 402a' overlaps the flexible roof 106 when the digester 102 is empty and so that the second end slice 402b' overlaps the background 302 when the digester is full. In one embodiment, the dimensions of the sample region 402 and its placement within the image 400 should enable to flexible roof 106 to occupy the area between the first end slice 402a and the second end slice 402b when the flexible roof 106 stores biogas 116 within its desired amount of inflation, i.e., its desired operating capacity. For example, if a flexible roof 106 should be maintained between 80%-30% capacity to prevent overinflation and underinflation, then the sample region 402 should be selected with dimensions and placement within the image 400 so that when the flexible roof 106 is at a capacity at or between 80% and 30%, the flexible roof 106 is maintained within the central area of the sample region 402 between the first end slice 402a and the second end slice 402b.

Figure 5:
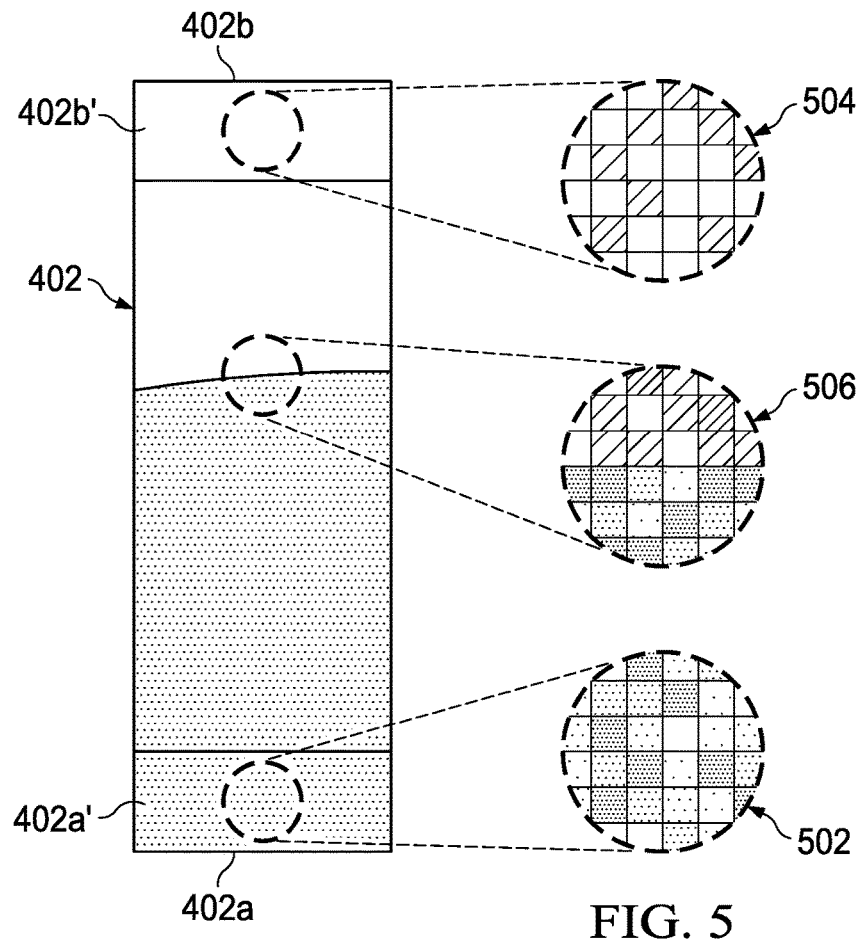
FIG. 5 is a schematic diagram depicting the sample region of the image and the pixels therein according to an illustrative embodiment.

The average color of the pixels in the first end slice 402a' and/or the second end slice 402b' can be determined, as described in more detail in FIGS. 5 and 6. Then, a comparison of test pixels in the remaining area of the sample region 402 between the first end slice 402a' and the second end slice 402b', or the test pixels throughout the entirety of the sample region 402, can be used to determine the percentage of the area of the sample region 402 occupied by the flexible roof 106 and/or the background 302, i.e., the fill percentages attributed to the flexible roof 106 and/or the background 302, respectively.

Because pixel color is used as the basis for determining the amount of the area of the sample region 402 occupied by objects within the image 400, placement of the sample region 402 within the image 400 should avoid objects that might be misinterpreted to be a part of the flexible roof 106. For example, in the image 400, the background structure 304 has a color similar to the flexible roof 106 and should be avoided. Further, the sample region 402 should be placed in a location with adequate contrast between the flexible roof 106 and the background 302. In some embodiments, where placement of the camera 104 cannot provide sufficient contrast between the flexible roof 106 and the background 302, a reference object 404 can be placed in the field of view for determining an amount of inflation of the flexible roof 106. The reference object 404 is shown behind the flexible roof 106, but in another embodiment, the reference object can be placed in front of the flexible roof 106. When utilizing a reference object e, the sample region 402 should be positioned and sized to include only the flexible roof 106 and the reference object 404.

FIG. 5 is a schematic diagram depicting the sample region of the image and the pixels therein according to an illustrative embodiment. The sample region 402 has a first end slice 402a' at the first end 402a, which only overlaps the flexible roof 106, and a second end slice 402b' at the second end 402b, which does not overlap the flexible roof 106. In this illustrative embodiment in FIG. 5, the second end slice 402b' only overlaps the background 302.

In one embodiment, the average pixel color of the flexible roof 106 can be determined by determining the RGB value for pixels 502 included in the first end slice 402a'. In particular, the average pixel color of the flexible roof 106 can be determined by calculating the average red value, the average green value, and the average blue value. The average red value can be calculated by summing each of the red values for the plurality of pixels 502 and dividing the result by the number of pixels in the plurality of pixels 502. The average green value can be calculated by summing each of the green values for the plurality of pixels 502 and dividing the result by the number of pixels in the plurality of pixels 502. The average blue value can be calculated by summing each of the blue values for the plurality of pixels 502 and dividing the result by the number of pixels in the plurality of pixels 502. The average pixel color of the background 302 can be determined similarly by determining the RGB value for each of the plurality of pixels 504 including in the second end slice 402b' and calculating an average red value, an average green value, and an average blue value.

The average pixel color for the flexible roof 106 can be compared with test pixels 506 in the sample region 402 to determine a fill percentage of the sample region 402 attributed to the flexible roof 106. In one embodiment, test pixels 506 is every pixel within the sample region 402. In another embodiment, test pixels 506 is every pixel in the area of sample region 402 between the first and second end slices 402a' and 402b'. In yet another embodiment, test pixels 506 can be a subset of every pixel within the sample region 402, or a subset of every pixel within the area between the first and second end slices 402a' and 402b', e.g., every N pixel, where N is an integer value. The average pixel color for the background 302 can also be compared with test pixels 506 in the sample region 402 to determine a fill percentage of the sample region 402 attributed to the background 302. In one embodiment, the fill percentages of the sample region 402 are determined by using an RGB three-dimensional array 600 as described in more detail in FIG. 6 that follows.

Figure 6A:
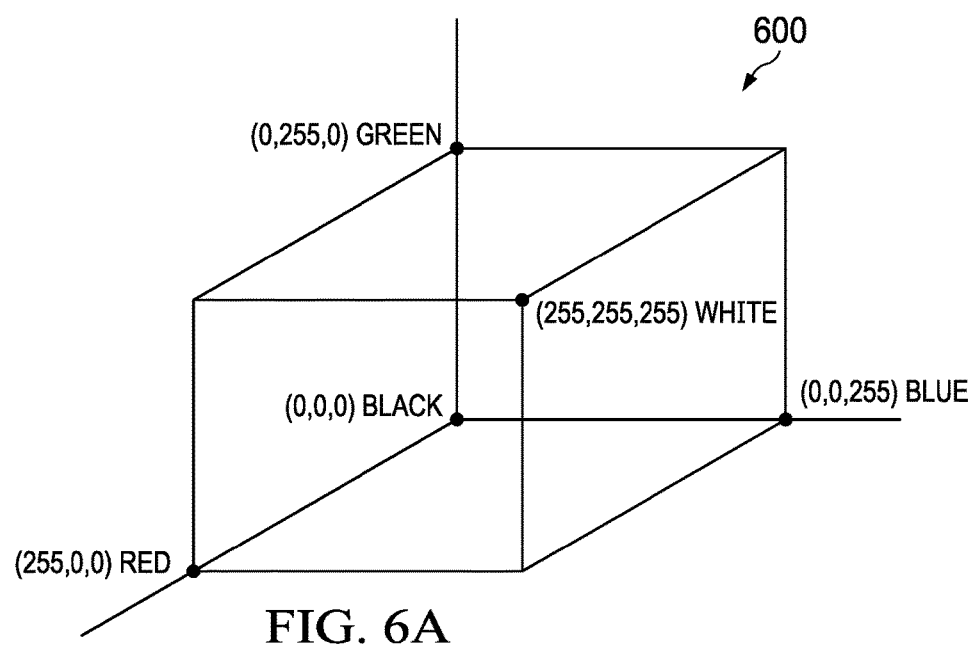
FIG. 6A is a diagram of an RGB three-dimensional color array according to an illustrative embodiment.

FIG. 6A is a diagram of an RGB three-dimensional color array according to an illustrative embodiment. The RGB 3-D array 600 is formed from three axes, with the x-axis corresponding to red, the y-axis corresponding to green, and the z-axis corresponding to blue. Thus, a pixel at (255,0,0) is red, a pixel at (0,255,0) is green, and a pixel at (0,0,255) is blue. Additionally, a pixel at (0,0,0) is black, and a pixel at (255,255,255) is white. In the alternative, these values can also be represented in hexadecimal. Thus, the red pixel can be located at #FF0000, the green pixel can be located at #00FF00, the blue pixel can be located at #0000FF, the black pixel can be located at #000000, and the white pixel can be located at #FFFFFF. The average pixel color of the flexible roof 106 and the average pixel color of the background 302 can be plotted on the RGB 3-D array 600 along with the RGB values of each of the test pixels within the sample region 402. The relative distances between the average pixel color of the flexible roof 106 and the test pixels can be used to determine a fill percentage of the sample region 402 attributed to the flexible roof 106, and the relative distances between the average pixel color of the background 302 and the test pixels can be used to determine a second fill percentage of the sample region 402 attributed to the background 302, as described in more detail in the figure that follows.

Figure 6B:
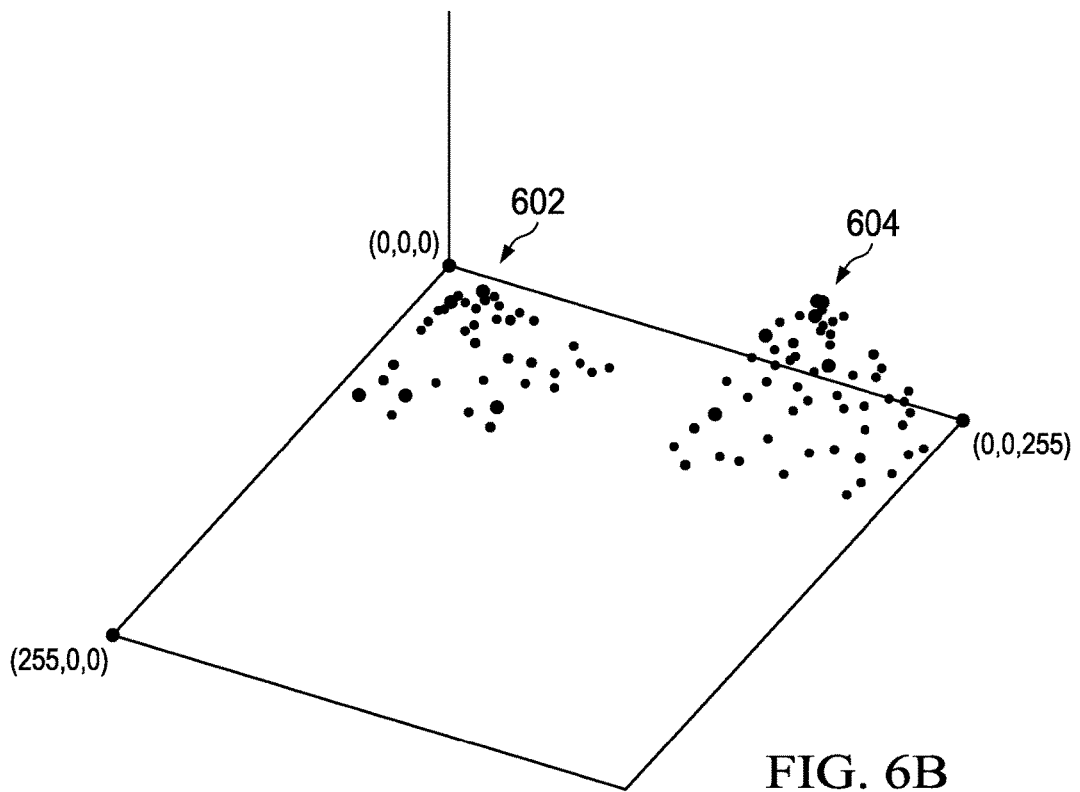
FIG. 6B is a diagram of pixels plotted in the RGB three-dimensional color array for determining fill percentages according to an illustrative embodiment.

FIG. 6B is a diagram of pixels of the first end slice 402a' and the second end slice 402b' plotted in the RGB three-dimensional array according to an illustrative embodiment. In particular, the pixels of the flexible roof 106 form a first three-dimensional curve 602, and the pixels of the background 302 form a second three-dimensional curve 604. The average pixel color of the flexible roof 106 and background 302 can be determined numerically or graphically and generally correspond with the peaks of curves 602 and 604, respectively. The average pixel color of the flexible roof 106 and the background 302 can be compared with the colors of the test pixels 506 to determine which of the test pixels 506 are attributed to the flexible roof 106 or the background 302.

Figure 6C:
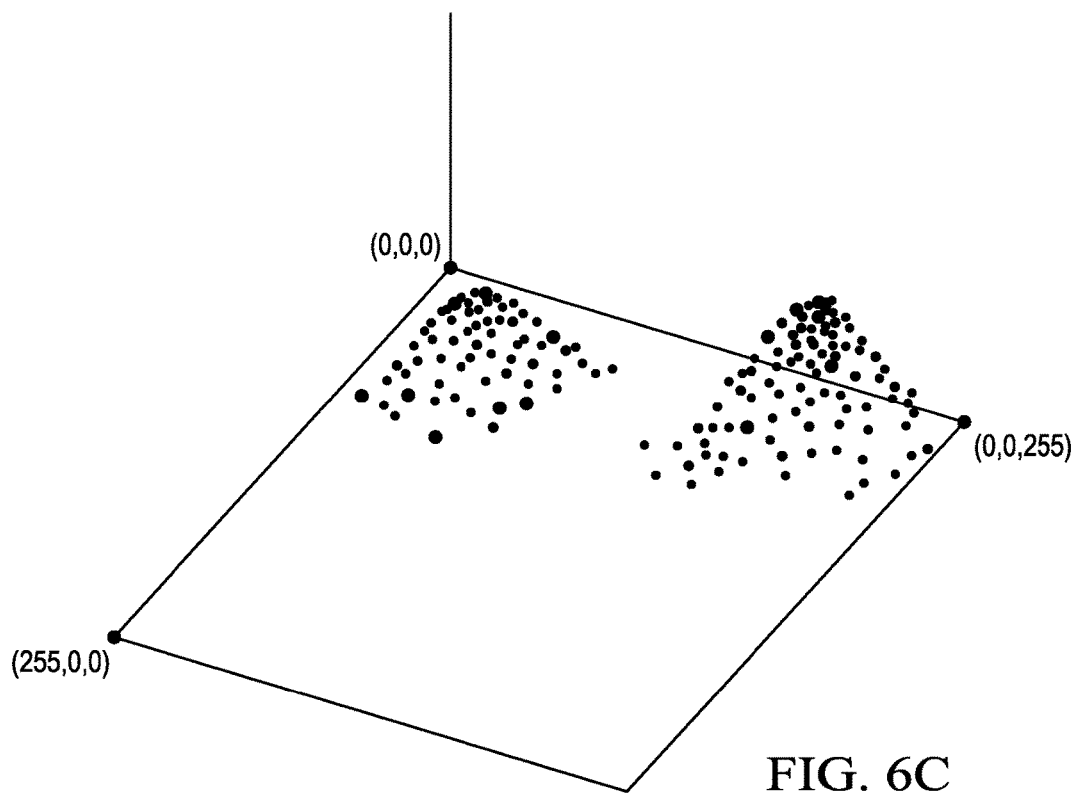
FIG. 6C is a diagram depicting test pixels plotted in the RGB three-dimensional color array in accordance with an illustrative embodiment.
Figures 6D, 7:
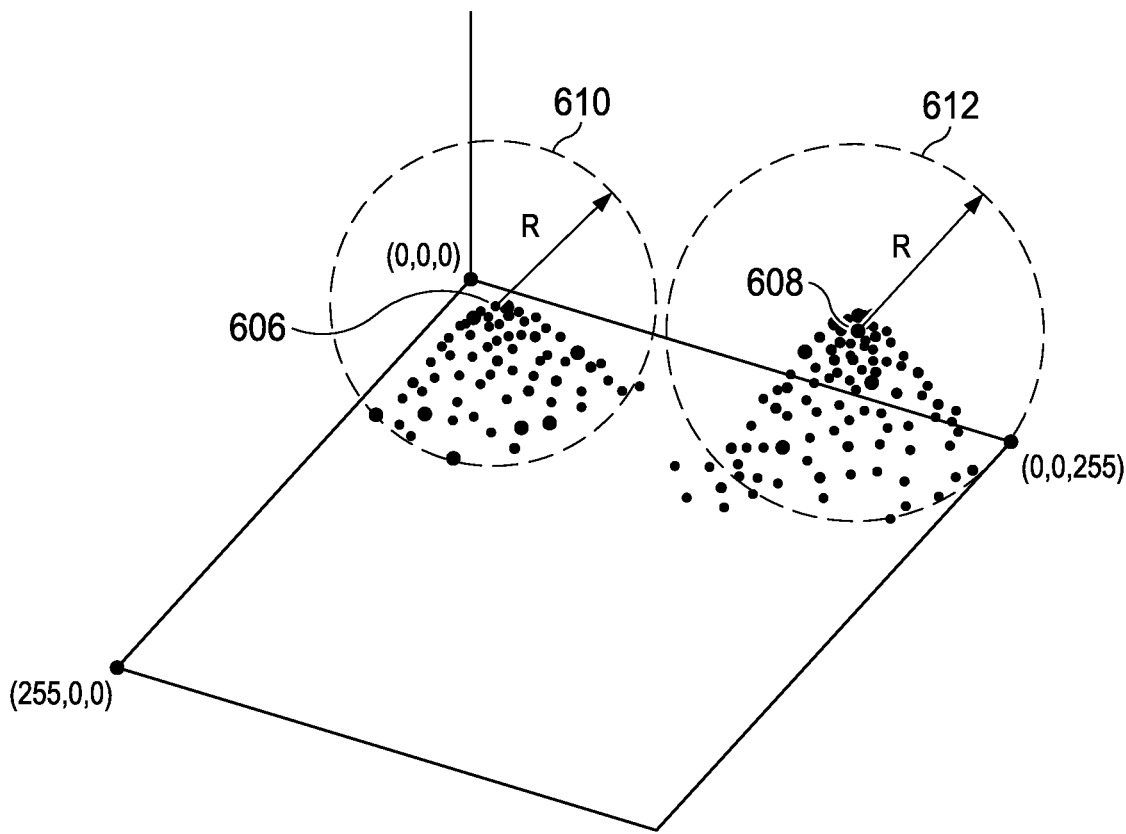
FIG. 6D is a diagram depicting test pixels plotted in the RGB three-dimensional color array, which comport with a color tolerance factor in accordance with an illustrative embodiment.
FIG. 7 is a table depicting calibration data for extraction of biogas from a digester according to an illustrative embodiment.

In one embodiment, the test pixels 506 are plotted in the RGB three-dimensional array, as shown in FIG. 6C. In FIG. 6D, the pixel 606 is the average pixel color of the flexible roof 106, which is positioned relatively closely to the origin because the flexible roof 106 is often formed from dark sheets of polymeric membrane. Pixel 608, the average pixel color of the background 302, is located closer to light blue because the background 302 in the various embodiments of this disclosure is the sky.

To determine the fill percentage of the sample region 402 attributed to the flexible roof 106, vectors can be generated that extend between the average roof pixel color 606 and the RGB values of each of the test pixels in the RGB 3-D array 600. A magnitude of the vectors can be determined, which indicates the relative distance between the average roof pixel color 606 and each of the test pixels. The test pixels that are within a predefined distance R from the average roof pixel color 606 are attributed to the flexible roof 106. The predefined distance R is a constant value that is equal to a color tolerance factor that can be a default value or user-provided value. The totality of all test pixels that could be attributed to the flexible roof 106 would be enclosed within the sphere with a radius R extending from the average roof pixel 606. In a non-limiting embodiment, the fill percentage of the sample region 402 attributed to the flexible roof 106 can be calculated by dividing the number of test pixels enclosed by the sphere 610 of radius R by the number of pixels within the sample region 402. Additionally, the fill percentage of the background 302 can be calculated from the fill percentage of the flexible roof 106 based on the selection of the sample region 402 to include only the flexible roof 106 and the background 302. For example, if the flexible roof 106 is determined to cover 70% of the sample region 402, i.e., the flexible roof 106 has a fill percentage of 70%, then the background 302 has a fill percentage of 30%.

To determine the fill percentage of the sample region 402 attributed to the background 302, vectors can be generated that extend between the average background pixel color 608 and the RGB values of each of the test pixels in the RGB 3-D array 600. A magnitude of the vectors can be determined, which indicates the relative distance between the average background pixel color 608 and each of the test pixels. The test pixels that are within a predefined distance R from the average background pixel color 608 are attributed to the background 302. The totality of all test pixels that could be attributed to the background 302 would be enclosed within the sphere 612 with a radius R extending from the average background pixel 608. In a non-limiting embodiment, the fill percentage of the sample region 402 attributed to the background 302 can be calculated by dividing the number of test pixels enclosed by sphere 612 by the number of pixels within the sample region 402. Additionally, the fill percentage of the sample region 402 attributed to the background 302 can be used to determine the fill percentage of the flexible roof 106, i.e., the background 302 has a fill percentage of 20%, then the background 302 has a fill percentage of 80%, as previously described.

Thus, in one embodiment, the fill percentage of the sample region 402 attributed to the flexible roof 106 can be used to directly calculate the amount of inflation of the flexible roof 106. In another embodiment, the fill percentage of the sample region 402 attributed to the background 302 can be used to indirectly calculate the amount of inflation of the flexible roof, e.g., subtracting the fill percentage of the background 302 from 100% to obtain the fill percentage of the flexible roof 106. In yet another embodiment, the fill percentage of the flexible roof 106 can be calculated from the fill percentages obtained directly and indirectly. For instance, in the examples above, the fill percentage of the flexible roof 106 calculated directly yielded a fill percentage of 70%, and the fill percentage of the flexible roof 106 calculated indirectly yielded a fill percentage of 80%. A total image match estimate can be calculated by averaging the two values, e.g., (70+80)÷2=75%.

A confidence factor can also be calculated by the inflation estimation program 804 from the fill percentage of the sample region 402 attributed the flexible roof 106 and the second fill percentage attributed to the background 302. In one embodiment, the confidence factor is calculated by subtracting the fill percentage and the second fill percentage from 1 and dividing by 100 to obtain a percentage. The confidence factor can be used to for validation of the algorithm, showing the degree of agreement between the analysis attributed to the flexible roof and the analysis attributed to the background. The confidence factor can be calculated during the calibration process to confirm whether the placement of the sample region 402 is acceptable. If the confidence factor falls outside of an acceptable threshold, then the sample region 402 can be placed elsewhere. The confidence factor can also be calculated during biogas production outside of the calibration process to determine whether the estimated amount of inflation should be deemed valid or if the estimate amount of inflation should be deemed invalid so that alternate means of estimating the amount of inflation should be utilized.

In another embodiment, the average pixel color of the flexible roof 106 can be determined by determining the RGB value for each of the plurality of pixels 502 that are included in the first end slice 402a' and then utilizing statistical analysis to determine the average color for the flexible roof 106. Likewise, the average pixel color of the background 302 and can be determined by determining the RGB value for each of the plurality of pixels 504 that are included in the second end slice 402b' and then utilizing statistical analysis to determine the average pixel color for the background 302. Once the average pixel color(s) is/are determined, then the relative amount of an object within the sample region 402, i.e., the flexible roof 106 and/or the background 302, can be determined by comparing test pixels within the sample region 402 with the average pixel color(s). In one embodiment, test pixels that fall within a predefined standard deviation from the average pixel color of the flexible roof 106 can be attributed to the flexible roof, and test pixels that fall within a predefined standard deviation from the average pixel color of the background 302 can be attributed to the background 302. The predefined standard deviation, also referred to herein as a color tolerance factor, can be a default constant value or a user-defined constant value. In this embodiment, a fill percentage attributed to the flexible roof 106 can be determined by a ratio of the number of pixels within the predefined standard deviation of the average pixel color of the flexible roof 106 and the number of pixels in the first end slice 402a'. A fill percentage attributed to the background 302 can be determined by a ratio of the number of pixels within the predefined standard deviation of the average pixel color of the background 302 and the number of pixels in the second end slice 402b'. A total image match estimate and a confidence factor can also be calculated, as previously described.

During the calibration process, a user identifies a sample region 402 within an image 300 that includes a flexible roof 106 and another object, such as a background 302, and the inflation estimation program 804 determines fill percentages of the sample region 402 attributed to the flexible roof 106 and optionally second fill percentages of the sample region 402 attributed to the background 302. If confidence factors indicate that placement of the sample region 402 is acceptable, then fill percentages are determined when an amount of inflation of the flexible roof 106 is varied according to predetermined values to generate calibration data that can be used to determine amounts of inflation during biogas production outside of the calibration process. The amount of inflation can be varied by allowing known volumes of biogas to collect under the flexible roof 106 or by providing estimated inflation percentages between 0-100% full. An example of the calibration data is provided in the figure that follows.

FIG. 7 is a table including calibration data according to an illustrative embodiment. The calibration data 700 is depicted in table format and can be stored in a network accessible storage device, such as storage device 814 in FIG. 1, and usable by an inflation estimation program 804 for controlling extraction of biogas from a digester. However, in other embodiments, the calibration data 700 can be stored in an alternate data structure and maintained locally to the inflation estimation program 804.

The calibration data 700 depicted in FIG. 7 includes three columns of data: object fill percentage data 702, biogas volume data 704, and estimated roof inflation percentage data 706. In this illustrative embodiment, the biogas volume data 704 and the estimated roof inflation percentage data 706 may be referred to as amount of inflation data. In some embodiments, the calibration data 700 includes either biogas volume data 704 or estimated roof inflation percentage data 706, or both. As previously discussed, the amount of inflation data can be generated during a calibration period. For example, when the digester 102 is completely empty, analysis of a corresponding image of the digester 102 can indicate that the flexible roof 106 occupies approximately 10% of the sample region 402, a correlation that is shown in the first row of calibration data 700. The amount of biogas within the digester 102 can then be varied according to known amounts, as indicated by onsite equipment, and if included in calibration data 700, estimates of the roof inflation percentage can also be provided, e.g., by operators visually inspecting the flexible roof 106. These values can then be correlated with fill percentages of the flexible roof 106 by analyzing corresponding images taken of the digester 102. Exemplary results are shown in calibration data 700.

After the calibration data 700 has been generated, the inflation estimation program 804 can analyze newly captured images of the digester 102 with reference to the calibration data 700 for determining an amount of inflation of the flexible roof 106, which can be referenced for extraction biogas from the digester 102. In particular, a subsequently captured image of the digester 102 can be analyzed to determine a real-time fill percentage for one or more objects in the image. Using the real-time fill percentage, the inflation estimation program 804 can reference the calibration data 700 to find a corresponding amount of inflation from biogas volume data 704 and/or estimated roof inflation percentage data 706. Thereafter, the inflation estimation program 804 can transmit the amount of inflation and estimated biogas volume to an operator for controlling biogas extraction from the digester 102.

In some embodiments, the amount of inflation of the flexible roof 106 can be used as feedback for automatically controlling the extraction of biogas 116 from the digester 102. For example, if the amount of inflation is below a certain threshold, then the biogas collection system 100 can allow the digester 102 to continue filling with biogas 116. If the amount of inflation is above that certain threshold, then the biogas collection system 100 can begin extracting biogas 116 from the digester 102. The inflation estimation program 804 can analyze the amount of inflation of the flexible roof 106 on a predetermined, periodic basis, such as every 8 hours. In addition, or in the alternative, a remote user can instruct the inflation estimation program 804 to analyze the amount of inflation of the flexible roof 106 aperiodically.

Figure 8:
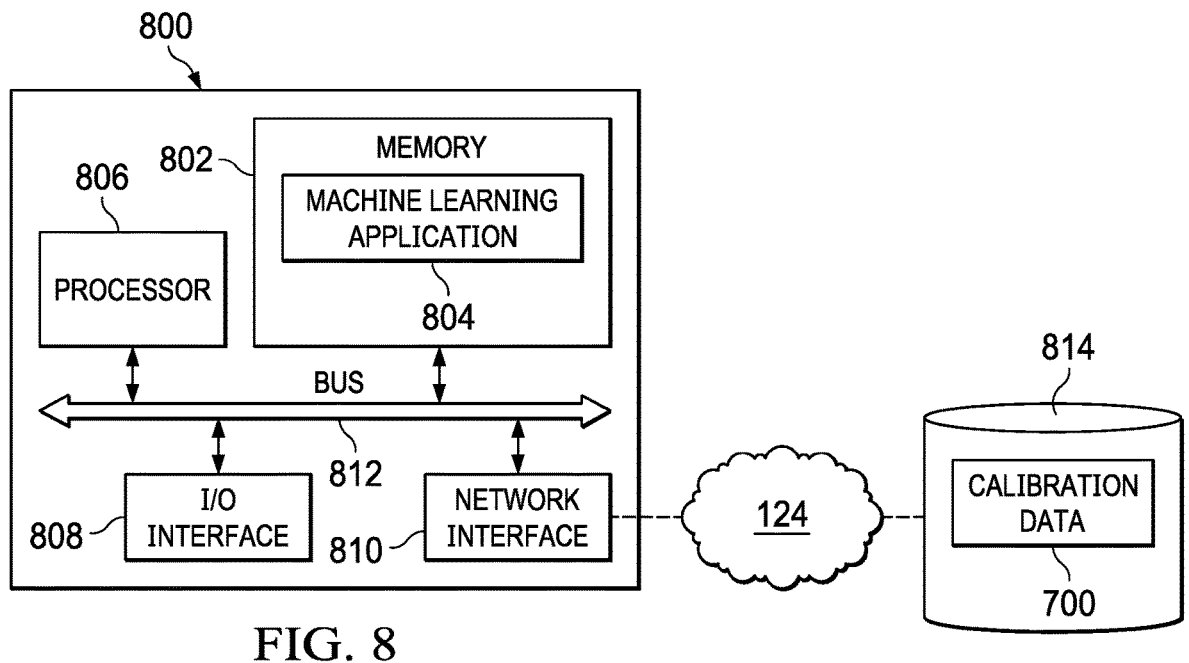
FIG. 8 is an example of a computing device for hosting an inflation estimation program configured to control the extraction of biogas from a digester in accordance with an illustrative embodiment.

FIG. 8 is an example of a computing device for hosting an inflation estimation program configured to control the extraction of biogas in accordance with an illustrative embodiment. In this illustrative embodiment, computing device 800 is implemented as a remote server communicatively coupled with network 124.

The computing device 800 includes memory 802 storing an inflation estimation program 804 that can be executed by processor 806 to automatically control onsite equipment for extraction of biogas 116. The processor 806 can include one or more processors, CPUs, microcontrollers, FPGAs, ASICs, DSPs, or any combination of the above.

The computing device 800 can be controlled locally by input/output devices (e.g., keyboard, mouse, monitor) via the I/O interface 808. The computing device 800 can also be controlled remotely via the network interface 810. The network interface 810 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater. The components of computing device 800 can be interconnected via a bus 812.

Figure 9:
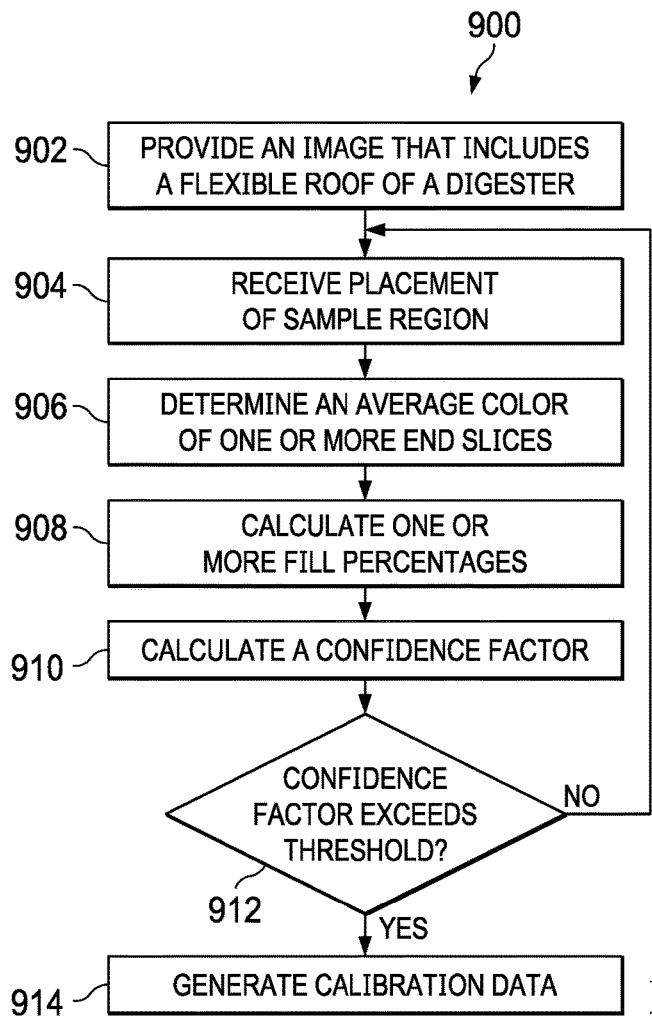
FIG. 9 is a flowchart of a calibration process in accordance with an illustrative embodiment.

FIG. 9 is a flowchart of a calibration process in accordance with an illustrative embodiment. Steps of flowchart 900 can be implemented in an electronic device, such as computing device 800 or remote client computing device 126.

Flowchart 900 begins at Step 902 by providing an image that includes a flexible roof of a digester and a background, such as image 300 that includes the flexible roof 106 of digester 102 and a background 302. In Step 904, a sample region placement is received. In one embodiment, the sample region placement is defined by receiving a reference point and a set of dimensional parameters and optionally an orientation of the sample region. In some embodiments, the end slices of the sample region are defined automatically based on the dimensional parameters of the sample region. For example, each end slice can be a predetermined percentage of the total size of the sample region and positioned automatically at opposing ends of the sample region. Alternatively, the dimensional parameters of the end slice can also include a parameter to define the size of the end slices, which are also automatically positioned at the first end and the second end in this alternative embodiment. In a non-limiting embodiment, the sample region is placed in the image so that an end slice at a first end overlaps the flexible roof of the digester when the digester is empty and so that a second end slice at the second end overlaps the background when the digester is full. In Step 906, an average color of a first end slice at the first end of the sample region and a second end slice at the second end of the sample region are calculated. In Step 908 fill one or more fill percentages can be calculated to determine a percentage of the sample region attributed to the flexible roof. In one embodiment, a total image match estimate is calculated. In Step 910, a confidence factor is calculated. In Step 912, a determination is made as to whether the confidence factor exceeds a predetermined threshold. If the confidence factor does not exceed the predetermined threshold, then flowchart 900 returns to Step 904. However, if the confidence factor does exceed the predetermined threshold, then calibration data is generated in Step 914. In one embodiment, the calibration data is generated by varying an amount of inflation of the flexible roof of the digester and determining corresponding fill percentages.

Figure 10:
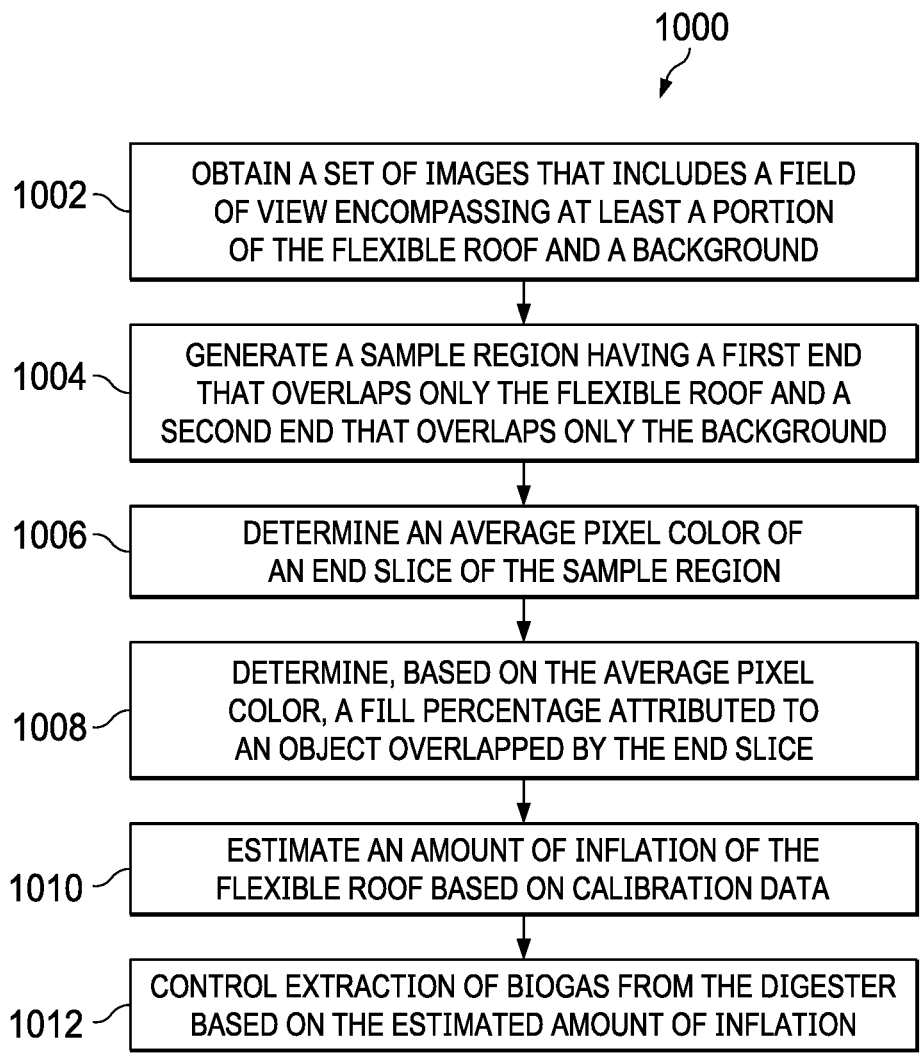
FIG. 10 is a flowchart of a process for extraction of biogas from a digester according to an illustrative embodiment.

FIG. 10 is a flowchart of a process for controlling the extraction of biogas from a digester in accordance with an illustrative embodiment. The process in flowchart 1000 can be implemented by an inflation estimation program, such as inflation estimation program 804 in FIG. 8.

Flowchart 1000 begins at Step 1002 by obtaining a set of images that includes a field of view encompassing at least a portion of the flexible roof and a background.

In Step 1004, a sample region is generated having a first end that overlaps only the flexible roof and a second end that overlaps only the background. In a non-limiting embodiment, the sample region can be generated from a coordinate for a corner of the sample region, a height dimension and a width dimension, and a parameter indicating a size of the end slice. One or more of the coordinates for the corner of the sample region, the height dimension and the width dimension, and the parameter indicating a size of the end slice can be default values and/or user-defined.

In Step 1006, an average pixel color of an end slice is determined. The end slice can be located at the first end or the second end of the sample region. In a non-limiting embodiment, the average color for pixels in the end slice can be determined based on an RGB value for each pixel in the end slice.

In Step 1008, a fill percentage attributed to an object overlapped by the end slice is determined based on the average pixel color of the end slice of the sample region.

In Step 1010, an amount of inflation of the flexible roof is determined based on calibration data that correlates fill percentages with amounts of inflation. In some embodiments, the amount of inflation is the volume of biogas within the digester, and in other embodiments the amount of inflation is roof inflation estimation data.

In Step 1012, the amount of inflation is used for extraction of the biogas from the digester. In one embodiment, the amount of inflation used as a feedback metric for automatic extraction of biogas, and in another embodiment the amount of inflation is presented to an operator for manually controlling extraction of biogas.

Figure 11:
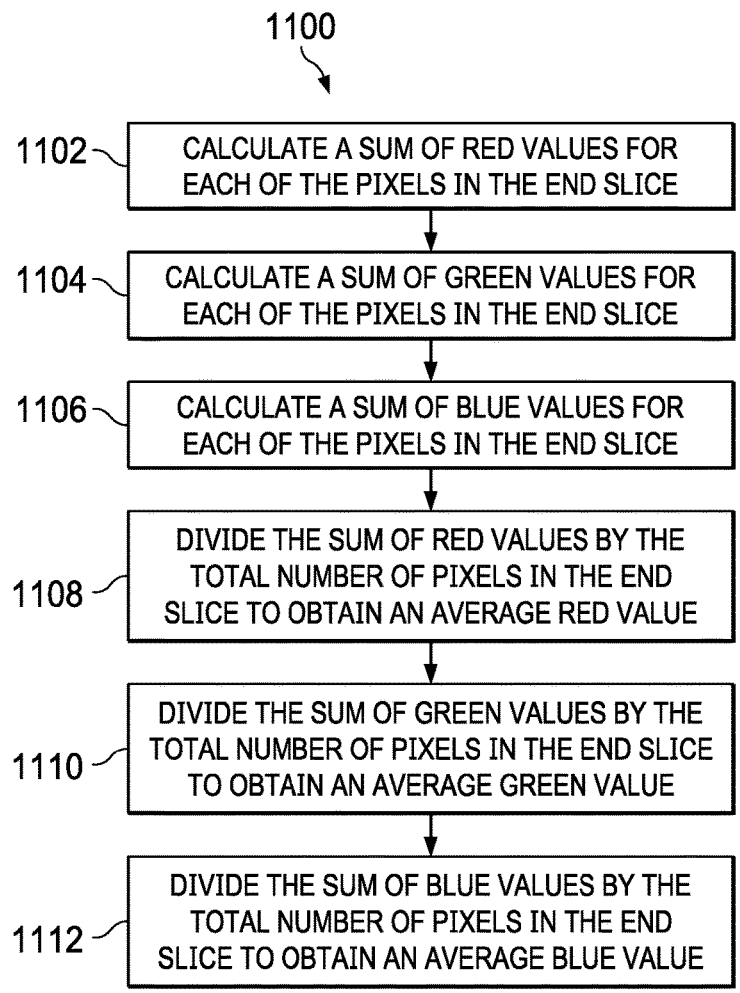
FIG. 11 is a flowchart of a process for determining an average color of pixels in a sample region according to an illustrative embodiment.

FIG. 11 is a flowchart of a process for determining the average pixel color of an end slice according to an illustrative embodiment. The process in flowchart 1100 can be implemented by a inflation estimation program, such as inflation estimation program 804 in FIG. 8, at Step 1006 in flowchart 1000.

Flowchart 1100 begins at Step 1102, where a sum of red values for each of the pixels in the end slice are calculated.

In Step 1104, a sum of blue values for each of the pixels in the end slice are calculated.

In Step 1106, a sum of green values for each of the pixels in the end slice are calculated.

In Step 1108, the sum of red values is divided by the total number of pixels in the end slice to obtain an average red value.

In Step 1110, the sum of blue values is divided by the total number of pixels in the end slice to obtain an average blue value.

In Step 1112, the sum of green values is divided by the total number of pixels in the end slice to obtain an average green value. The average pixel color of the end slice is the average red value, the average blue value, and the average green value.

Figure 12:
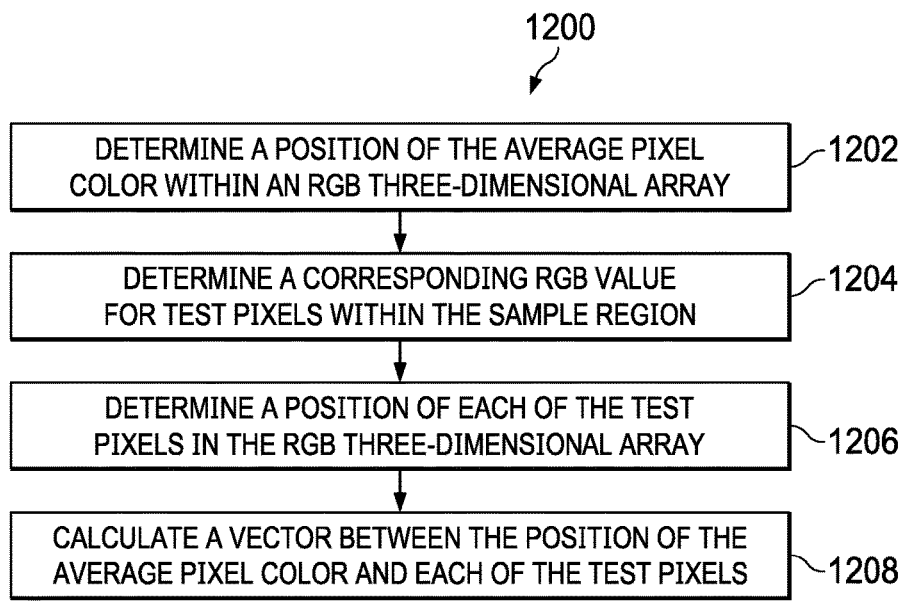
FIG. 12 is a flowchart of a process for determining fill percentages of the sample region according to an illustrative embodiment.

FIG. 12 is a flowchart of a process for determining fill percentages of the sample region according to an illustrative embodiment. The process in flowchart 1200 can be implemented by an inflation estimation program, such as inflation estimation program 804 in FIG. 8, at Step 1008 in flowchart 1000.

Flowchart 1200 begins at Step 1202 by determining a position of the average pixel color within a red, green, blue (RGB) three-dimensional (3-D) array.

In Step 1204, a corresponding RGB value is determined for test pixels within the sample region.

In Step 1206, a position of each of the test pixels within the RBG three-dimensional array is determined based on the corresponding RBG value.

In Step 1208, a vector is calculated between the position of the average pixel color and each of the test pixels. The fill percentage of the sample region is based on a number of the test pixels separated from the average pixel color by a magnitude less than a color tolerance factor. In a non-limiting embodiment, the fill percentage of the sample region is a ratio of the number of the test pixels separated from the average pixel color by the magnitude less than the color tolerance factor and the number pixels within sample region.

In a non-limiting embodiment, where fill percentages are calculated based on the end slice, which can be located at the first end of the sample region, and a second end slice, which can be located at the second end of the sample region, the Flowchart 1200 can include a step of determining a second average pixel color for pixels in a second end slice of the sample region based on an RGB value for each pixel in the second end slice. Flowchart 1200 can also include a step of determining a second fill percentage of the sample region attributed to the background. The second fill percentage of the sample region is based on a relative position of the second average pixel color within the RGB three-dimensional array and the corresponding RGB value for test pixels within the sample region. Further, the second fill percentage is based on a number of test pixels separated from the second average pixel color by a magnitude less than the color tolerance factor.

While this invention has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method for controlling biogas extraction, the method comprising:
   obtaining a set of images that includes a field of view encompassing at least a portion of a flexible roof and a background;

generating a sample region having a first end that overlaps only the flexible roof and a second end that overlaps only the background;
determining an average pixel color of an end slice of the sample region, wherein the end slice is located at the first end or the second end of the sample region;
determining, based on the average pixel color of the end slice of the sample region, a fill percentage of the sample region attributed to an object overlapped by the end slice;
estimating an amount of inflation of the flexible roof based on the fill percentage and a correlation between fill percentages of the sample region and predetermined amounts of inflation included in calibration data; and
controlling extraction of the biogas based on the estimated amount of inflation.

2. The method of claim 1, wherein generating the sample region further comprises:
receiving a coordinate for a corner of the sample region;
receiving a height dimension and a width dimension; and
receiving a parameter indicating a size of the end slice, and
wherein the sample region is generated based on the coordinate for the corner, the height dimension, the width dimension, and the parameter indicating the size the end slice.

3. The method of claim 1, wherein determining the average pixel color of the end slice further comprises:
determining an average color for pixels in the end slice based on a red, green, blue (RGB) value for each pixel in the end slice.

4. The method of claim 3, wherein determining the average pixel color of the end slice further comprises:
calculating a sum of red values for each of the pixels in the end slice;
calculating a sum of blue values for each of the pixels in the end slice;
calculating a sum of green values for each of the pixels in the end slice; and
dividing the sum of red values by a total number of pixels in the end slice to obtain an average red value;
dividing the sum of blue values by the total number of pixels in the end slice to obtain an average blue value; and
dividing the sum of green values by the total number of pixels in the end slice to obtain an average green value,
wherein the average color for pixels in the end slice is the average red value, the average blue value, and the average green value.

5. The method of claim 4, wherein determining the fill percentage of the sample region attributed to the object that is overlapped by the end slice further comprises:
determining a position of the average pixel color within an RGB three-dimensional array;
determining a corresponding RGB value for test pixels within the sample region;
determining a position of each of the test pixels within the RBG three-dimensional array based on the corresponding RBG value; and
calculating a vector between the position of the average pixel color and each of the test pixels,
wherein the fill percentage of the sample region is based on a number of the test pixels separated from the average pixel color by a magnitude less than a color tolerance factor.

6. The method of claim 5, wherein the fill percentage of the sample region is a ratio of the number of the test pixels separated from the average pixel color by the magnitude less than the color tolerance factor and the number pixels within the sample region.

7. The method of claim 6, wherein the end slice is located at the first end of the sample region overlapping the flexible roof and wherein the method further comprises:
determining a second average pixel color for pixels in a second end slice of the sample region based on an RGB value for each pixel in the second end slice, wherein the second end slice is located at the second end of the sample region overlapping the background;
determining a second fill percentage of the sample region attributed to the background, wherein the second fill percentage of the sample region is based on a relative position of the second average pixel color within the RGB three-dimensional array and the corresponding RGB value for test pixels within the sample region, and wherein the second fill percentage is based on a number of test pixels separated from the second average pixel color by a magnitude less than the color tolerance factor.

8. The method of claim 7, wherein the second fill percentage is a ratio of the number of the test pixels separated from the second average pixel color by the magnitude less than the color tolerance factor and the number pixels within the sample region, and wherein the method further comprises:
calculating a total image match estimate based on an average of the fill percentage and the second fill percentage.

9. The method of claim 8, further comprising:
calculating a confidence of the total image match based on the fill percentage and the second fill percentage.

10. The method of claim 1, further comprising:
generating the calibration data by correlating fill percentages with predetermined amounts of inflation.

11. An apparatus comprising:
a processor;
a memory operatively connected with the processor, the memory storing instructions that, when executed by the processor, causes the apparatus to:
obtain a set of images that includes a field of view encompassing at least a portion of a flexible roof and a background;
generate a sample region having a first end that overlaps only the flexible roof and a second end that overlaps only the background;
determine an average pixel color of an end slice of the sample region, wherein the end slice is located at the first end or the second end of the sample region;
determine, based on the average pixel color of the end slice of the sample region, a fill percentage of the sample region attributed to an object overlapped by the end slice;
estimate an amount of inflation of the flexible roof based on the fill percentage and a correlation between fill percentages of the sample region and predetermined amounts of inflation included in calibration data; and
control extraction of the biogas based on the estimated amount of inflation.

12. The apparatus of claim 11, wherein the instructions to generate the sample region further comprises instructions that, when executed by the processor, causes the apparatus to:
receive a coordinate for a corner of the sample region;
receive a height dimension and a width dimension; and receive a parameter indicating a size of the end slice, and
wherein the sample region is generated based on the coordinate for the corner, the height dimension, the width dimension, and the parameter indicating the size the end slice.

13. The apparatus of claim 11, wherein the instructions to determine the average pixel color of the end slice further comprises instructions that, when executed by the processor, causes the apparatus to:
determine an average color for pixels in the end slice based on a red, green, blue (RGB) value for each pixel in the end slice.

14. The apparatus of claim 13, wherein the instructions to determine the average pixel color of the end slice further comprises instructions that, when executed by the processor, causes the apparatus to:
calculate a sum of red values for each of the pixels in the end slice;
calculate a sum of blue values for each of the pixels in the end slice;
calculate a sum of green values for each of the pixels in the end slice; and
divide the sum of red values by a total number of pixels in the end slice to obtain an average red value;
divide the sum of blue values by the total number of pixels in the end slice to obtain an average blue value; and
divide the sum of green values by the total number of pixels in the end slice to obtain an average green value,
wherein the average color for pixels in the end slice is the average red value, the average blue value, and the average green value.

15. The apparatus of claim 14, wherein the instructions to determine the fill percentage of the sample region attributed to the object that is overlapped by the end slice further comprises instructions that, when executed by the processor, causes the apparatus to:
determine a position of the average pixel color within an RGB three-dimensional array;
determine a corresponding RGB value for test pixels within the sample region;
determine a position of each of the test pixels within the RBG three-dimensional array based on the corresponding RBG value; and
calculate a vector between the position of the average pixel color and each of the test pixels,
wherein the fill percentage of the sample region is based on a number of the test pixels separated from the average pixel color by a magnitude less than a color tolerance factor.

16. The apparatus of claim 15, wherein the fill percentage of the sample region is a ratio of the number of the test pixels separated from the average pixel color by the magnitude less than the color tolerance factor and the number pixels within the sample region.

17. The apparatus of claim 16, wherein the end slice is located at the first end of the sample region overlapping the flexible roof and wherein the instructions comprise further instructions that, when executed by the processor, cause the apparatus to:
determine a second average pixel color for pixels in a second end slice of the sample region based on an RGB value for each pixel in the second end slice, wherein the second end slice is located at the second end of the sample region overlapping the background;
determine a second fill percentage of the sample region attributed to the background, wherein the second fill percentage of the sample region is based on a relative position of the second average pixel color within the RGB three-dimensional array and the corresponding RGB value for test pixels within the sample region, and wherein the second fill percentage is based on a number of test pixels separated from the second average pixel color by a magnitude less than the color tolerance factor.

18. The apparatus of claim 17, wherein the second fill percentage is a ratio of the number of the test pixels separated from the second average pixel color by the magnitude less than the color tolerance factor and the number pixels within the sample region, and wherein the instructions comprise further instructions that, when executed by the processor cause, the apparatus to:
calculate a total image match estimate based on an average of the fill percentage and the second fill percentage.

19. The apparatus of claim 18, wherein the instructions comprise further instructions that, when executed by the processor, cause the apparatus to:
calculate a confidence of the total image match based on the fill percentage and the second fill percentage.

20. The apparatus of claim 11, wherein the instructions comprise further instructions that, when executed by the processor, cause the apparatus to:
generate the calibration data by correlating fill percentages with predetermined amounts of inflation.

* * * * *